United States Patent
Hesseling et al.

(10) Patent No.: US 6,752,833 B2
(45) Date of Patent: Jun. 22, 2004

(54) PLUG FOR INSERTION INTO A BONE CANAL

(75) Inventors: Saret Cornelis Hesseling, Alphen a/d Rijn (NL); Petrus Tarasius Josephus Spierings, Nijmegen (NL)

(73) Assignee: IsoTis N.V., Bilthoven (NL)

( * ) Notice: Subject to any disclaimer, the term of this patent is extended or adjusted under 35 U.S.C. 154(b) by 39 days.

(21) Appl. No.: 10/047,433

(22) Filed: Jan. 15, 2002

(65) Prior Publication Data

US 2002/0111693 A1 Aug. 15, 2002

Related U.S. Application Data

(63) Continuation of application No. PCT/NL01/00134, filed on Feb. 19, 2001.

(30) Foreign Application Priority Data

| Feb. 18, 2000 | (EP) | ............................................. 00200565 |
| Feb. 18, 2000 | (EP) | ............................................. 00200566 |
| Oct. 12, 2000 | (EP) | ............................................. 00203547 |

(51) Int. Cl.⁷ .................................................. A61F 2/28
(52) U.S. Cl. ................................................. 623/23.48
(58) Field of Search .......................... 623/23.48, 16.11, 623/20.35, 20.36, 22.15, 23.58; 606/95, 72, 76, 78

(56) References Cited

U.S. PATENT DOCUMENTS

| 3,908,201 A | 9/1975 | Jones et al. .......................... 3/1 |
| 4,245,359 A | 1/1981 | Stuhmer .......................... 3/1.9 |
| 5,171,275 A | * 12/1992 | Ling et al. ..................... 623/16 |
| 5,263,991 A | 11/1993 | Wiley ............................. 623/66 |
| 5,383,932 A | 1/1995 | Wilson et al. ................. 623/16 |
| 5,766,178 A | 6/1998 | Michielli et al. ............. 606/95 |
| 5,879,403 A | 3/1999 | Ostiguy et al. ................ 623/22 |
| 6,280,477 B1 | * 8/2001 | Mastrorio et al. ....... 623/23.48 |

FOREIGN PATENT DOCUMENTS

| EP | 1027897 | 8/2000 |
| EP | 1038538 | 9/2000 |
| FR | 2758977 | 8/1998 |
| FR | 2763500 | 11/1998 |
| FR | 2776917 | 10/1999 |
| WO | WO 97/25940 | 7/1997 |

OTHER PUBLICATIONS

English abstract of FR 2758977.
English abstract of FR 2763500.
English abstract of FR 2776917.

* cited by examiner

Primary Examiner—Eduardo C. Robert
Assistant Examiner—David Comstock
(74) Attorney, Agent, or Firm—Banner & Witcoff, Ltd.

(57) ABSTRACT

A plug for insertion into a bone canal is disclosed. The plug comprises an elongate central body of substantially constant cross section carrying at least four radially extending flanges of substantially equal shape and size. The flanges form solid, disk-like structures, free of cuts and are axially spaced along the central axis of the body, such that they extend in substantially parallel planes. The plug is made of a copolymer of a polyalkylene glycol terephthalate and an aromatic polyester.

12 Claims, 5 Drawing Sheets

PLUG FOR INSERTION INTO A BONE CANAL

This application is a continuation of prior international application no. PCT/NL01/00134, filed on Feb. 19, 2001, which claims priority from European patent application number EP 00200565.0, filed Feb. 18, 2000; European patent application number EP 00200566.8 filed Feb. 18, 2000; and European patent application number EP 00203547.5 filed Oct. 12, 2000.

The invention relates to a plug for insertion in a bone canal.

Plugs for insertion into a bone canal are generally known and are used to restrict the flow of cement during prosthesis implantation.

In implant surgery and in particular for implantation of a hip prosthesis, it is common practice to cement the prosthesis to the bone. In order to cement the prosthesis to the bone, the bone canal is broached or reamed, such that the trabecular, porous bone portions are removed and the remaining cortical, hard bone portions define the walls of the bone canal. An anchoring portion of the prosthesis is then inserted into the bone canal, for example an anchoring portion of a hip prosthesis is inserted into a broached femoral bone, such that a ball portion of the prosthesis extends outward to replace the natural ball portion of the hip bone.

In order to fix the anchoring portion of the prosthesis to the bone, cement, such as polymethylmethacrylate (PMMA) is inserted into the bone canal and is packed upon the prosthesis prior to insertion thereof. This cement then anchors the anchoring portion of the prosthesis to the bone material.

In order to provide for a secure joint between the prosthesis and the bone at the cement interface, it is desired to have the cement completely surround the prosthesis in the interstices between the prosthesis and the bone material. However, the insertion forces and pressures exerted during insertion of the implant often drive the cement substance down into the intramedullary canal and away from the fixation area. This way, voids are formed in the cement mantle which later become stress points leading to early fatigue of the prothesis and/or the fixation.

In order to restrict the flow of bone cement further into the intramedullary canal, intramedullary plugging devices or "plugs" have been developed which can be inserted into the bone canal as a blockage. Usually, the plug is provided with fins or other flange-like projections. These fins or flanges serve for simultaneous fixing of the plug in the bone canal by clamping engagement of the walls and for blocking cement passage of the bone canal. When the implant is forced into the broached portion of the intramedullary canal, the tendency of the restricted bone cement to flow down the canal is prevented by the fins or flanges of the plug cooperating with the walls of the canal.

A problem associated with the known plugs is that the fins or flanges do not always cooperate sufficiently sealingly or blockingly with the bone canal. This is largely caused by the fact that the bone canal as defined by the cortical bone has a cross-section that varies along its longitudinal axis. In particular, the cross-section is of substantially elliptical or oval shape at the onset of the canal and axially inwardly becomes more circularly shaped at a midportion. Further inwardly, the cross-section becomes substantially oval or elliptically shaped again, having an orientation that is rotated around the axis of the canal to a position wherein it is substantially perpendicular to the orientation of the first section. In addition, for each person, the size of the bone and therewith the cross-section and axial dimension of the bone canal varies.

During implantation, the plug has to be placed sealingly at a predetermined location within the bone canal, e.g. about 1.5 cm axially inward from the preferred location of the lower tip of the anchoring portion after insertion.

Due to the varying shape of the bone canal it has proven difficult to provide a plug that can be used to reliably plug the canal at any axial location. Depending on the circumstances, a good chance exists that cement can either pass the flanges of the plug or that the plug can escape inwardly into the canal upon insertion of the anchoring portion.

In the prior art, to overcome the problem of insufficient cooperation of the flanges with the bone canal, it has been suggested to provide the plug with a plurality of flanges, each having varying radial dimension e.g. by tapering a central body from which disk-like fins extend as described in U.S. Pat. No. 5,383,932 or by providing a central body with disk-like fins of increasing size extend as described in U.S. Pat. No 5,879,403. This solution however has the disadvantage that the chance exists that one or more flange will not engage the wall sufficiently strong enough, which may cause the plug to escape into the canal. In addition, in the prior art it has been proposed to provide the flanges with radial cuts, such that insertion of such flanges into unexpectedly narrow portions of the bone canal is facilitated. An example thereof is shown in e.g. U.S. Pat. No. 4,245,359 or 5,766,178.

However, this increases the chance of cement passing through the flanges of the plug as the top surfaces of the flanges are open.

The invention aims to provide a plug in which the above problem is alleviated. According to the invention, providing a plug for insertion into a bone canal is provided, comprising an elongate central body of substantially constant cross section carrying at least four radially extending flanges of substantially equal shape and size, the flanges forming disk-like structures and being axially spaced along the central axis of the body, such that the extend in substantially parallel planes, the plug being made of a copolymer of a polyalkylene glycol terephtalate and an aromatic polyester.

Surprisingly, it has been found that a copolymer of polyalkylene glycol terephtalate and aromatic polyester allows for a plug configuration having a plurality of axially spaced, identical flanges, without the need for providing the flanges with a decreasing radial dimension. The at least four flanges each have equal chance of engaging the wall of the bone canal. The specific combination of configuration and material allows the flanges to cooperate both sufficiently sealingly and blockingly with the walls of the bone canal, while yet being made of a biocompatible and biodegradable material. Any radial cuts in the flanges may, in use be closed due to swelling of the material in response to surrounding fluid.

To further enhance flexibility, at least one of the flanges may be provided with at least one flexing zone having reduced material thickness relative to a supporting zone that surrounds the flexing zone. In particular, the flanges may be provided with apertures, which may or may not extend axially through the flanges. Examples of apertures that do not axially extend through the flanges are closed chambers or voids, blind holes and grooves. Examples of apertures that do axially extend through the flanges are perforations, through holes and slots. Due to swelling of the material, apertures extending axially through the flanges may in use may be at least partially closed, e.g. in case of an axially tapered perforation in a flange.

The flexibility of the material also allows the flanges to be provided with a closed surface, free of cuts. This reduces the chance of leakage to a minimum. In particular, the flanges may be free of any apertures that in use extend through the flanges in axial direction Preferably, the copolymer comprises 20–90 wt. %, more preferably 50–80 wt. % of the polyalkylene glycol terephthalate, and 80–10 wt. %, more preferably 50–20 wt. % of the aromatic polyester. A preferred type of copolymers according to the invention is formed by the group of block copolymers.

The polyalkylene glycol terephthalate may have a weight average molecular weight of about 150 to about 4000. Preferably, the polyalkylene glycol terephthalate has a weight average molecular weight of 200 to 1500. The aromatic polyester preferably has a weight average molecular weight of from 200 to 5000, more preferably from 250 to 4000. The weight average molecular weight of the copolymer preferably lies between 10,000 and 300,000, more preferably between 40,000 and 120,000.

The weight average molecular weight may suitably be determined by gel permeation chromatography (GPC). This technique, which is known per se, may for instance be performed using chloroform as a solvent and polystyrene as external standard. Alternatively, a measure for the weight average molecular weight may be obtained by using viscometry (see NEN-EN-ISO 1628-1). This technique may for instance be performed at 25° C. using chloroform as a solvent. Preferably, the intrinsic viscosity of the copolymer lies between 0.2289 and 1.3282 dL/g, which corresponds to a weight average molecular weight between 10,000 and 200,000. Likewise, the more preferred ranges for the weight average molecular weight measured by GPC mentioned above can also be expressed in terms of the intrinsic viscosity.

In a preferred embodiment, the polyalkylene glycol terephthalate component has units of the formula —OLO—CO—Q—CO—, wherein O represents oxygen, C represents carbon, L is a divalent organic radical remaining after removal of terminal hydroxyl groups from a poly(oxyalkylene)glycol, and Q is a divalent organic radical.

Preferred polyalkylene glycol terephthalates are chosen from the group of polyethylene glycol terephthalate, polypropylene glycol terephthalate, and polybutylene glycol terephthalate and copolymers thereof, such as poloxamers. A highly preferred polyalkylene glycol terephthalate is polyethylene glycol terephthalate.

The terms alkylene and polyalkylene generally refer to any isomeric structure, i.e., propylene comprises both 1,2-propylene and 1,3-propylene, butylene comprises 1,2-butylene, 1, 3-butylene, 2, 3-butylene, 1,2-isobutylene, 1,3-isobutylene and 1,4-isobutylene (tetramethylene) and similarly for higher- alkylene homologues. The polyalkylene glycol terephthalate component is preferably terminated with a dicarboxylic acid residue —CO—Q—CO—, if necessary to provide a coupling to the polyester component. Group Q may be an aromatic group having the same definition as R, or may be an aliphatic group such as ethylene, propylene, butylene and the like.

The polyester component preferably has units —O—E—O—CO—R—CO—, wherein O represents oxygen, C represents carbon, E is a substituted or unsubstituted alkylene or oxydialkylene radical having from 2 to 8 carbon atoms, and R is a substituted or unsubstituted divalent aromatic radical.

In a preferred embodiment, the polyester is chosen from the group of polyethylene terephthalate, polypropylene terephthalate, and polybutylene terephthalate. A highly preferred polyester is polybutylene terephthalate.

The preparation of the copolymer will now be explained by way of example for a polyethylene glycol terephthalate/polybutylene terephthalate copolymer. Based on this description, the skilled person will be able to prepare any desired copolymer within the above described class. An alternative manner for preparing polyalkylene glycol terephthalate/polyester copolymers is disclosed in U.S. Pat. No. 3,908,201.

A polyethylene glycol terephtalate/polybutylene terephthalate copolymer may be synthesized from a mixture of dimethyl terephthalate, butanediol (in excess), polyethylene glycol, an antioxidant and a catalyst. The mixture is placed in a reaction vessel and heated to about 180° C., and methanol is distilled as transesterification proceeds. During the transesterification, the ester bond with methyl is replaced with an ester bond with butylene and/or the polyethylene glycol. After transesterification, the temperature is raised slowly to about 245° C., and a vacuum (finally less than 0.1 mbar) is achieved. The excess butanediol is distilled off and a prepolymer of butanediol terephthalate condenses with the polyethylene glycol to form a polyethylene/polybutylene terephthalate copolymer. A terephthalate moiety connects the polyethylene glycol units to the polybutylene terephthalate units of the copolymer and thus such a copolymer also is sometimes referred to as a polyethylene glycol terephthalate/polybutylene terephthalate copolymer (PEGT/PBT copolymer).

Further preferred embodiments of the invention are described in the appended claims.

The invention will be elucidated further by means of drawings. In the drawings are:

The drawings are only schematic representations of an exemplary embodiment of the plug. In the drawings, identical or corresponding parts are identified with the same reference numerals.

Figure 1:
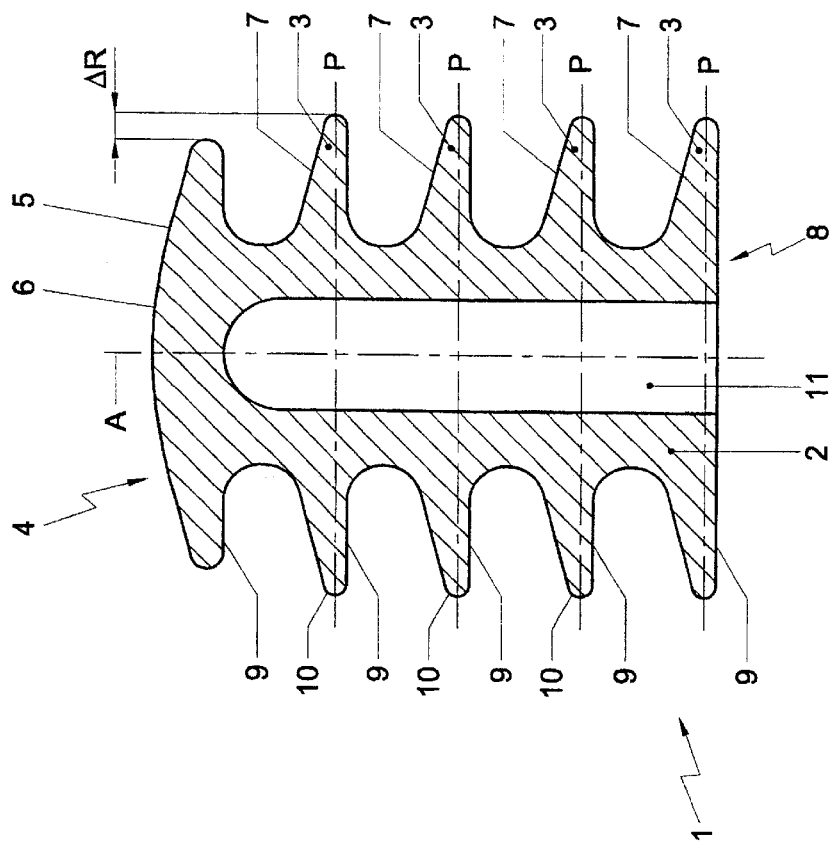
FIG. 1 shows a schematic cross sectional view of a bone plug.
Figure 2:
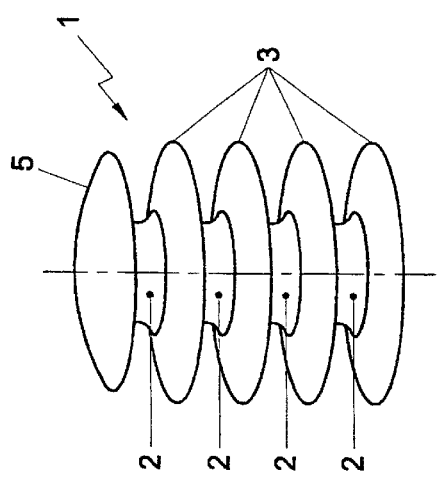
FIG. 2 shows a schematic perspective view of the bone plug of FIG. 1.

FIG. 1 and FIG. 2 show a plug 1 for insertion into a bone canal. The plug 1 comprises an elongate central body 2 of substantially constant cross section. The central body 2 carries four radially extending flanges of equal shape and size. The flanges 3 form solid, disk-like structures having a closed surface, free of cuts. The flanges 3 do not comprise any cuts and upon deformation, maintain a closed sealing surface. The flanges 3 are axially spaced along the central axis A of the body 1 and extend in substantially parallel planes P. The plug 1 is, as set out above, made of a copolymer of a polyalkylene glycol terephthalate and an aromatic polyester.

The central body 1 carries on a front portion 4 thereof a front flange 5. The front flange 5 has, relative to the other flanges 3, a smaller radial dimension. In the drawing, the difference is indicated by ΔR. This way, the front portion 4 of the plug 1 can be inserted more easily into a bone canal and will, upon insertion, provide a centering effect. To further facilitate insertion, the front flange 5 has a convex top surface 6. In the shown embodiment, the top surfaces 9 of the other flanges are also slightly curved or sloped in the direction of the rear end 8 of the plug during insertion. Preferably, the flanges 5, 3 have a substantially planar or rearwardly sloping bottom surface 9. In addition, the flanges 3, 5 are provided with rounded edges 10 extending from the top surfaces 6, 7 to the rear surfaces 9. This way, sealing engagement of the sidewalls of a bone canal is facilitated.

The plug 1 further comprises a blind bore 11, extending axially from a rear portion 8 of the plug towards the front portion 4. The blind bore 11 can be used to insert the tip of a tool 12 with which the plug 1 is inserted in an inserting direction 13 into a bone canal 14, as shown in FIG. 3.

Figure 3:
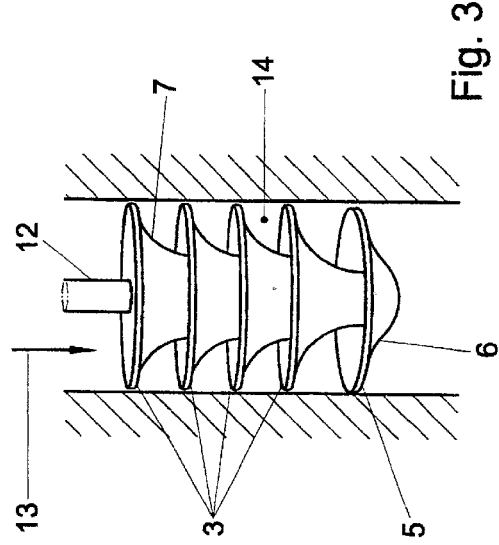
FIG. 3 shows a schematic cross sectional view of a portion of a bone canal in which the plug is inserted.

In FIG. 3 it is shown how, due to the combination of the configuration and the material of the plug 1, the plug 1 can deform to cooperate both sealingly and blockingly with the sidewalls of the bone canal.

Figure 4:
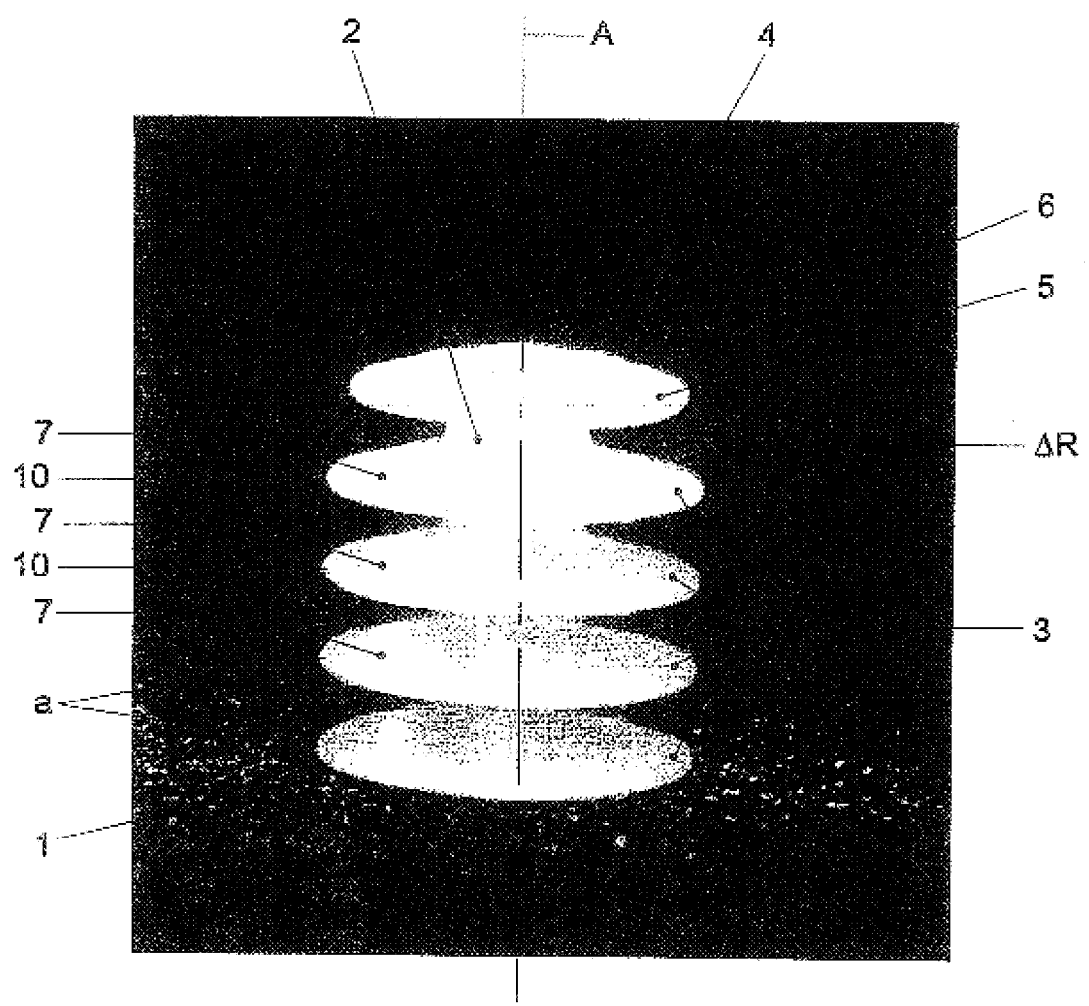
FIG. 4 shows a photograph of a bone plug corresponding to FIG. 1.

Referring to FIG. 4, a photograph is shown of the bone plug 1, analogous to the drawing shown in FIG. 2.

Figure 5:
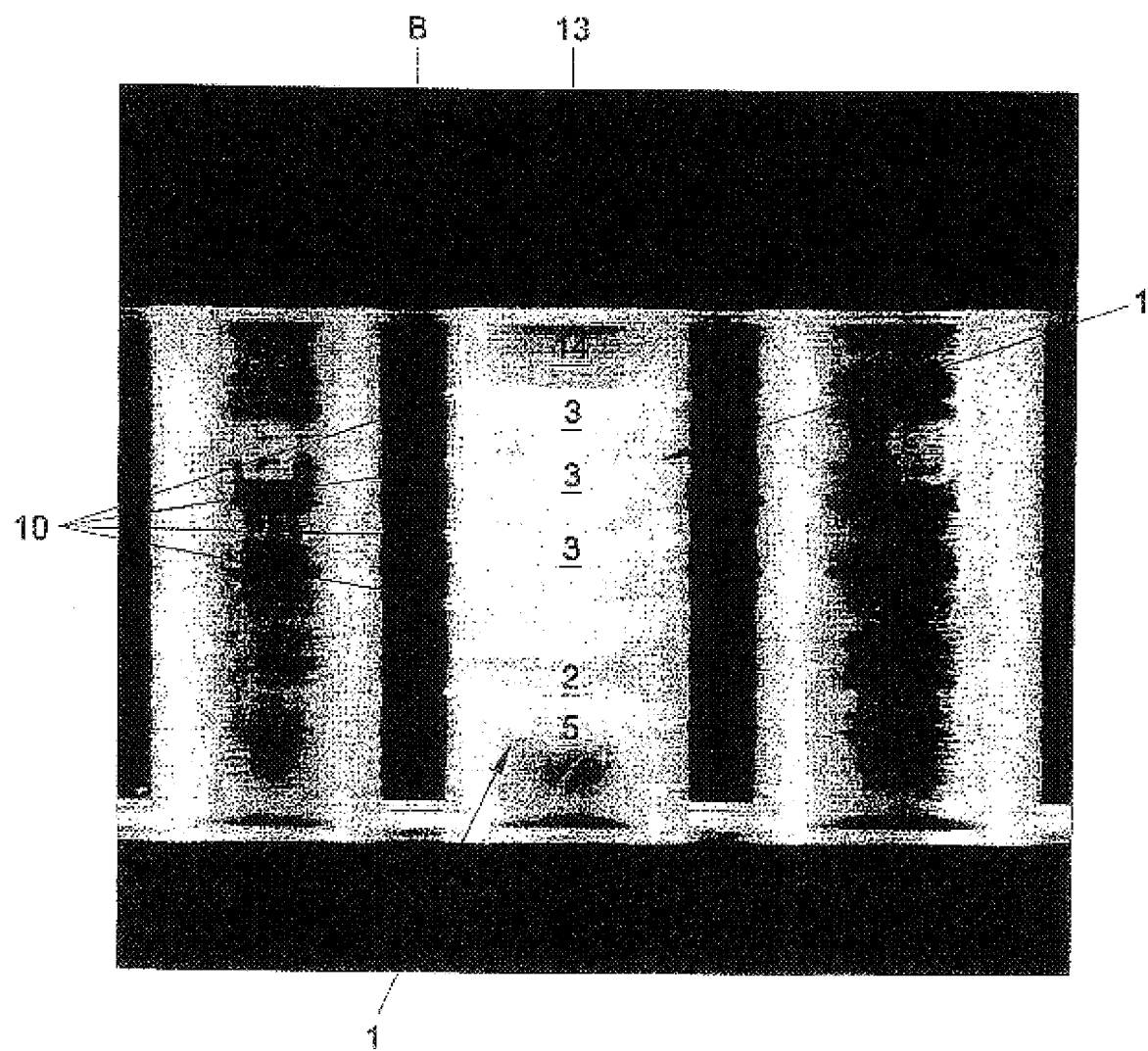
FIG. 5 shows a photograph of the bone plug of FIG. 4 inserted in a bore in a block of transparent material.

FIG. 5 shows a photograph of the bone plug 1 inserted into a cylindrical canal in a block B of transparent material.

Figure 6:
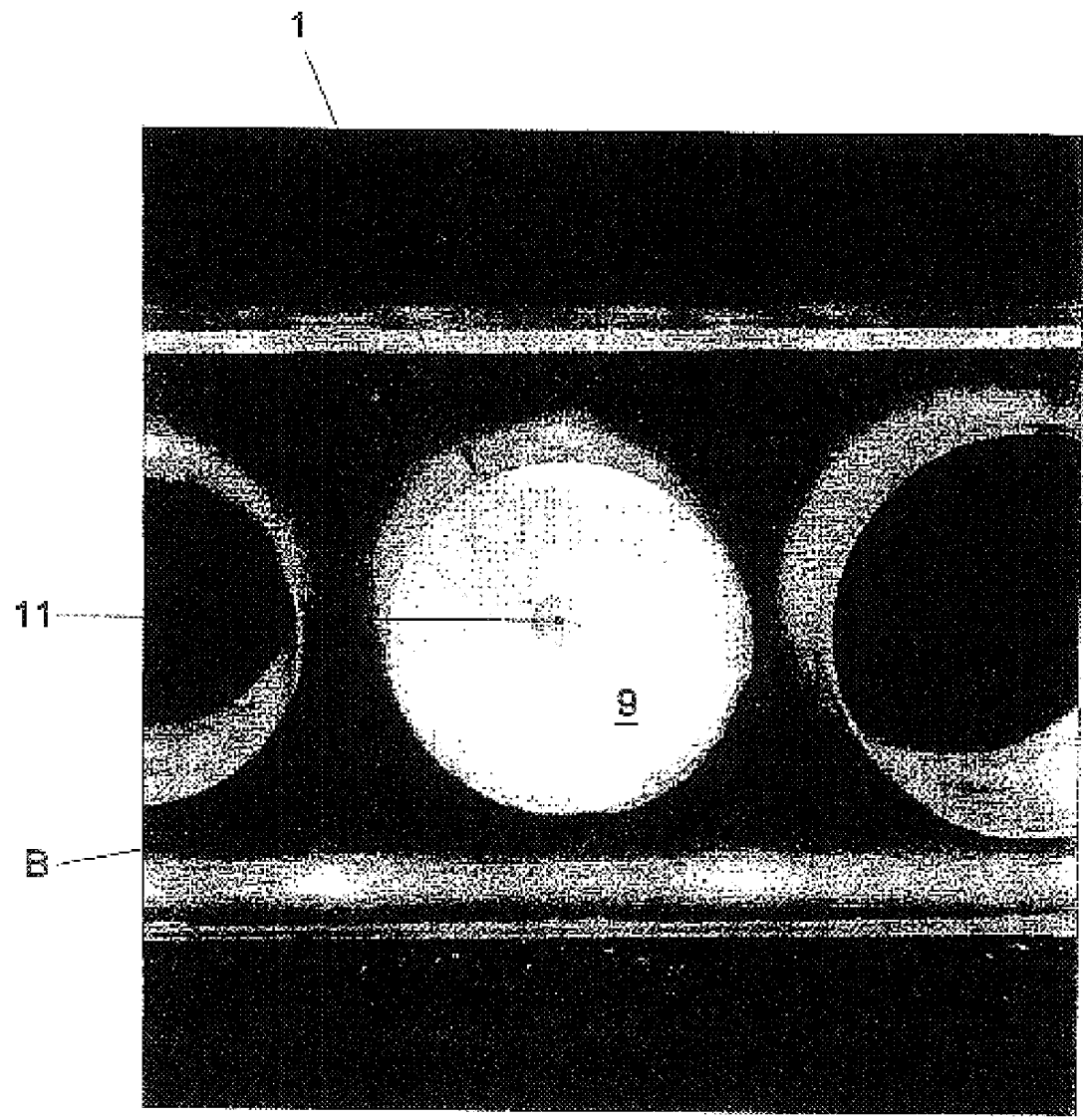
FIG. 6 shows a photographic top view of the block of FIG. 5.

FIG. 6 shows a photographic top view of the block of FIG. 5.

From FIGS. 5 and 6, it is clear that the flanges sealingly engage the walls of the bore in the block B. In FIG. 5 it is shown that the front flange 5, due to its smaller radial dimension, shows a lower degree of backward flexing than the other flanges 3. The top view of FIG. 6 shows the rear flange 3 having a closed surface, free of cuts.

Figure 7:
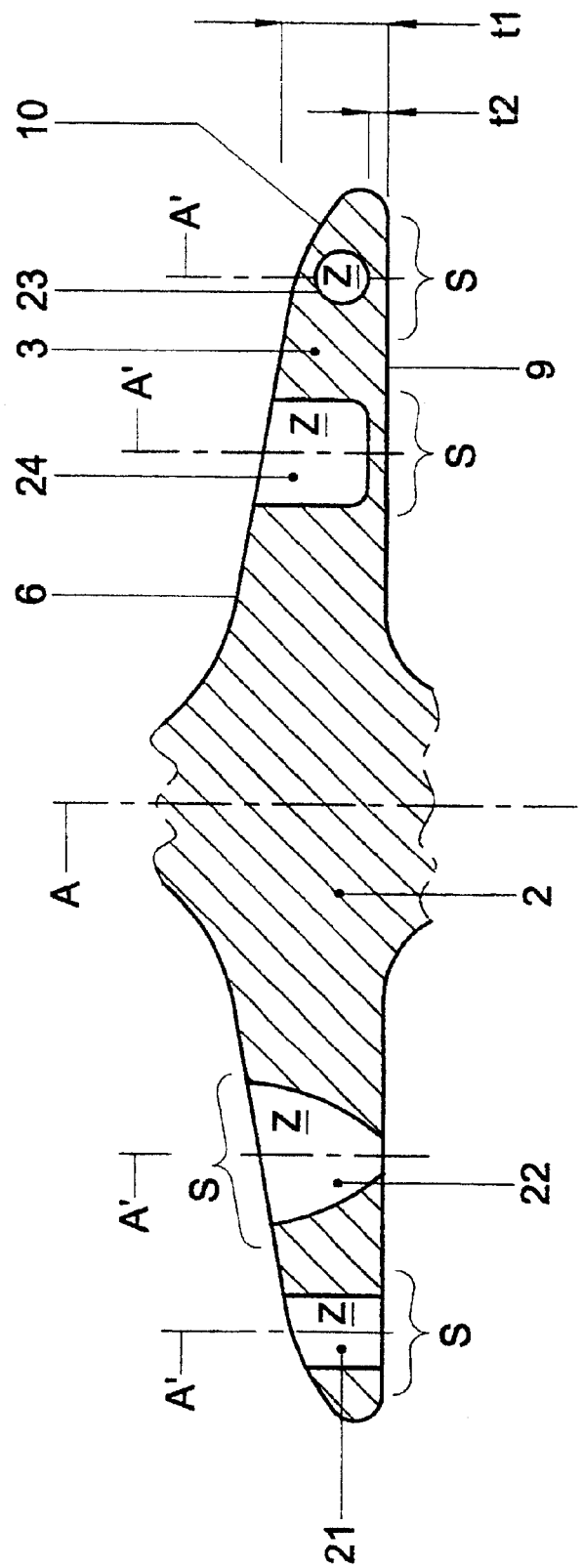
FIG. 7 shows a cross section of a flange having different types of flexing zones for enhancing flexibility of the flange.

As shown in FIG. 7, to further enhance flexibility, a flange 3 can be provided with several flexing zones Z having reduced material thickness t2 relative to the thickness t1 of the material at supporting zones S that surround the flexing zones Z. In particular, the flange 3 is provided with apertures that extend axially along axis A' through the flange 3 form the top surface 6 to the bottom surface 9, namely a straight trough hole 21 and an axially tapered perforation 22 which may close upon swelling of the material of the supporting zone S. In these cases, the thickness t2 of the material at the flexing zone Z is locally reduced to zero. Apertures that do not axially extend through the flange are also shown as a void 23 and a blind hole 24.

It shall be clear to the skilled man that the plug is not limited to the preferred embodiments described herein and that many variations are possible within the scope of the appended claims. For example, it is possible to provide the flanges with radial cuts. Such cuts may in use be closed due to the swellable behavior of the copolymer of polyalkylene glycol terephthalate and aromatic polyester.

In particular, it should be noted that the plugs can be used in bone cannals in various bones of the body, e.g. in an upper arm bone canal for a shoulder prosthesis or a lower leg bone canal for a knee prosthesis.

What is claimed is:

1. A plug for insertion into a bone canal, comprising an elongate central body of substantially constant cross section carrying at least four radially extending flanges of substantially equal shape and size, the flanges being axially spaced along the central axis of the body, such that they extend in substantially parallel planes, the plug being made of a copolymer of a polyalkylene glycol terephthalate and an aromatic polyester.

2. A plug according to claim 1, wherein at least one of the flanges is provided with at least one flexing zone having reduced material thickness relative to a supporting zone that surrounds the flexing zone.

3. A plug according to claim 1, wherein the flanges form solid, disk-like structures having a closed surface.

4. A plug according to claim 1, wherein the central body carries at least five radially extending flanges, and wherein a front flange carried on a front portion of the central body is, relative to the other flanges, provided with a smaller radial dimension.

5. A plug according to claim 3, wherein at least the front flange has a convexly curved top surface.

6. A plug according to claim 1, wherein the flanges comprise a substantially planar bottom surface.

7. A plug according to claim 1, wherein the flanges are provided with rounded edges.

8. A plug according to claim 1, wherein the central body is provided with a blind bore extending axially from a rear portion of the central body.

9. A plug according to claim 1, wherein the rear portion of the central body radially extends as the back surface of a flange.

10. A plug according to claim 1, wherein the polyalkylene glycol terephthalate is polyethylene glycol terephthalate and the aromatic ester is polybutylene terephthalate.

11. A plug according to claim 10, wherein the copolymer comprises from 20–90 wt. % of the polyethylene glycol terephthalate, based on the weight of the copolymer.

12. A plug according to claim 10, wherein the copolymer comprises from 50–80 wt. % of the polyethylene glycol terephthalate, based on the weight of the copolymer.

* * * * *